United States Patent [19]

Schenk et al.

[11] 4,316,862
[45] Feb. 23, 1982

[54] PROCESS FOR THE PREPARATION OF SULPHONIC ACID CHLORIDES

[75] Inventors: Wolfgang Schenk, Leverkusen; Heinz U. Blank, Odenthal; Ferdinand Hagedorn, Leverkusen; Werner Evertz, Monheim, all of Fed. Rep. of Germany

[73] Assignee: Bayer Aktiengesellschaft, Leverkusen, Fed. Rep. of Germany

[21] Appl. No.: 141,861

[22] Filed: Apr. 21, 1980

Related U.S. Application Data

[63] Continuation of Ser. No. 944,458, Sep. 21, 1978, abandoned.

[30] Foreign Application Priority Data

Sep. 28, 1977 [DE] Fed. Rep. of Germany ....... 2743540

[51] Int. Cl.³ .......................................... C07C 143/26
[52] U.S. Cl. .............................................. 260/543 R
[58] Field of Search .................................. 260/543 R

[56] References Cited

U.S. PATENT DOCUMENTS 4,105,692  8/1978  Blank ........................... 260/543 R
4,215,071  7/1980  Blank et al. .................. 260/543 R Primary Examiner—Paul J. Killos
Attorney, Agent, or Firm—Sprung, Felfe, Horn, Lynch & Kramer

[57] ABSTRACT

An improved process for the preparation of a sulphonic acid chloride of the formula

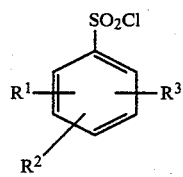
(I)

wherein $R^1$, $R^2$ and $R^3$ are identical or different and denote hydrogen, a lower alkyl radical or a cycloalkyl radical, halogen, aryl, aralkyl, aryl ether or a radical $-SO_2Cl$, $-SO_2aryl$,

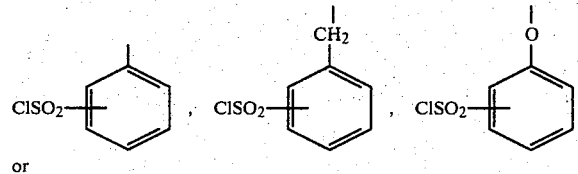

or

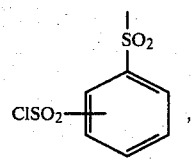

or wherein adjacent radicals $R^1$ and $R^2$ are linked to form a cycloaliphatic, aromatic or hetero-aromatic ring which is optionally substituted by a sulphonic acid chloride group by contacting an aromatic compound of the formula

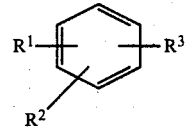

wherein $R^1$, $R^2$ and $R^3$ of the above-mentioned meaning, with chlorosulphonic acid and thionyl chloride, the improvement residing in employing initially approximately stoichiometric amounts of aromatic compound and chlorosulphonic acid, effecting reaction of the aromatic compound and chlorosulphonic acid and thereafter contacting the reaction product with excess thionyl chloride.

16 Claims, No Drawings

PROCESS FOR THE PREPARATION OF SULPHONIC ACID CHLORIDES

This is a continuation of application Ser. No. 944,458, filed Sept. 21, 1978, now abandoned.

The invention relates to a process for the preparation of sulphonic acid chlorides by reacting aromatic compounds with chlorosulphonic acid and thionyl chloride.

It is known (Ullmanns Enzyklopädie der technischen Chemie (Ullmann's Encyclopaedia of industrial Chemistry), 4th edition, volume 8 (1974), page 420) to prepare benzenesulphonyl chloride by reacting benzene with excess chlorosulphonic acid. The use of excess chlorosulphonic acid is a considerable disadvantage of this process, especially with respect to protection of the environment, since the excess chlorosulphonic acid is hydrolysed with water to hydrogen chloride and sulphuric acid during the working up of the reaction mixture and is obtained as so-called dilute acid, together with the sulphuric acid also additionally formed as a by-product and together with considerable amounts of benzenesulphonic acid which have not been converted into the sulphonic acid chloride. The working up and removal of this dilute acid unavoidably obtained leads to considerable expense. In the case of simple neutralisation of the dilute acid, a corresponding salt content in the effluent results, which is also undesirable for reasons of protection of the environment and makes expensive desalination of the effluent necessary.

A process has now been found for the preparation of sulphonic acid chlorides of the formula

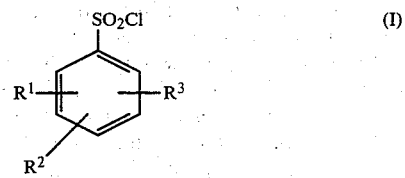

wherein $R^1$, $R^2$ and $R^3$ are identical or different and denote hydrogen, a lower alkyl radical or a cycloalkyl radical, halogen, aryl, aralkyl, aryl ether or a radical —$SO_2Cl$, —$SO_2aryl$,

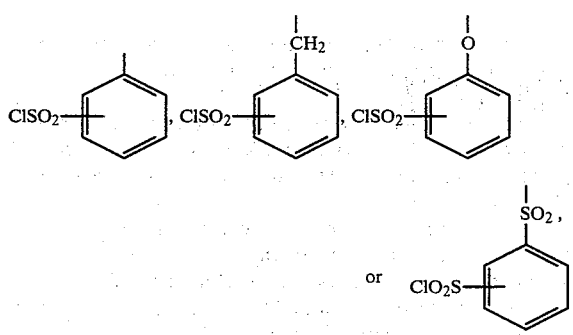

or wherein adjacent radicals $R^1$ and $R^2$ are linked to form a cycloaliphatic, aromatic or hetero-aromatic ring which is optionally substituted by a sulphonic acid chloride group, by reacting an aromatic compound of the formula

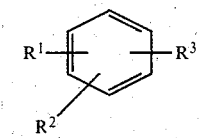

wherein $R^1$, $R^2$ and $R^3$ have the abovementioned meaning, with chlorosulphonic acid and thionyl chloride, in which approximately stoichiometric amounts of the aromatic compound and chlorosulphonic acid are first reacted, optionally in the presence of a solvent and optionally in the presence of a sulphonation auxiliary, and the product is then reacted with excess thionyl chloride.

Lower alkyl radicals ($R^1$ to $R^3$) can be straight-chain or branched alkyl radicals with 1 to 6, preferably 1 to 4, carbon atoms. Examples which may be mentioned are: methyl, ethyl, propyl, isopropyl, butyl, isobutyl, pentyl, isopentyl, hexyl and isohexyl.

Examples of cycloalkyl radicals ($R^1$ to $R^3$) which may be mentioned are cyclopentyl and cyclohexyl, preferably cyclohexyl.

Halogens ($R^1$ to $R^3$) which may be mentioned are fluorine, chlorine, bromine and iodine, preferably fluorine, chlorine and bromine.

Phenyl may be mentioned as an example of the aryl radicals ($R^1$ to $R^3$).

Examples of possible aralkyl radicals ($R^1$ to $R^3$) are those with 6 to 18 carbon atoms, the aliphatic part of which contains 1 to 6 carbon atoms and the aromatic part of which is a radical from the benzene series. The following araliphatic radicals may be mentioned as examples: benzyl, β-ethyl-phenyl, γ-propyl-phenyl and β-phenyl-n-hexyl, preferably benzyl.

An aryl ether radical ($R^1$ to $R^3$) which may be mentioned is, in particular, the phenoxy radical.

Fused ring systems, such as indane, tetralin and naphthalene, preferably naphthalene, are formed by the linking of the adjacent radicals $R^1$ and $R^2$ to give a cycloaliphatic or aromatic ring.

One can, of course, for the radicals $R^1$ to $R^3$ employ further substituted radicals. Examples which may be mentioned include halogen, lower alkyl, aryl, aroxy, alkoxy and aralkyl.

Preferred aromatic compounds which may be mentioned are compounds of the formula

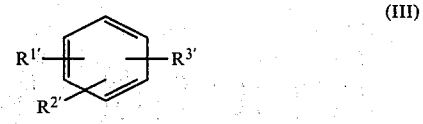

wherein $R^{1'}$, $R^{2'}$ and $R^{3'}$ are identical or different and denote hydrogen, an alkyl radical with 1 to 4 carbon atoms, fluorine, chlorine, bromine, phenyl, —$SO_2Cl$, —$SO_2phenyl$, phenoxy or benzyl, or wherein adjacent radicals $R^{1'}$ and $R^{2'}$ are linked to form a cycloaliphatic, aromatic or hetero-aromatic ring with 5 or 6 ring members.

The following aromatic compounds may be mentioned as examples: benzene, toluene, ethylbenzene, isopropylbenzene (cumene), tetralin, o-xylene, m-xylene, p-xylene, diphenyl, diphenylmethane, chlorobenzene, 1-chloronaphthalene, 2-chloronaphthalene, o-chlorotoluene, 1,2-, 1,3- and 1,4-dichlorobenzene, 2,3-, 2,4-, 2,5-, 3,4- and 2,6-dichloro-touene, 2,3-, 2,4-, 2,6-, 3,4- and 2,5-dimethylchlorobenzene, bromobenzene, fluorobenzene, 1,2,3- and 1,2,4-trichlorobenzene, diphenyl ether, naphthalene, 1- and 2-methylnaphthalene and 2-, 3- and 4-bromotoluene, diphenylsulphone, benzenesulphonyl chloride, toluenesulphonyl chloride, diphenylene sulphone and diphenylene oxide. The reaction of benzene is particularly preferred.

In a preferred embodiment, the process according to the invention can be carried out in the presence of a sulphonation auxiliary. In general, sulphonation auxiliaries in the process according to the invention are compounds which can act as Lewis bases towards chlorosulphonic acid.

Examples of sulphonation auxiliaries which may be mentioned are:

1. Carboxylic acids and their derivatives (for example acetic acid, propionic acid, butyric acid, pivalic acid, valeric acid, caproic acid, adipic acid, azelaic acid, halogenated carboxylic acids, such as mono-, di- and trichloroacetic acid, acetic anhydride, propionic anhydride, butyric anhydride, succinic anhydride, phthalic anhydride, acetyl chloride, propionyl chloride, butyryl chloride, adipyl chloride, acetic acid methyl ester, ethyl ester and butyl ester, propionic acid esters, butyric acid esters, formamide, dimethylformamide, phthalimide and succinimide), 2. Urea and alkylureas, 3. Phosphorus compounds (for example phosphoric acid and organic phosphorus derivatives, such as triethyl, trimethyl and tributyl phosphate and triethyl and trimethyl phosphite), 4. Ethers (for example diethyl ether, dioxane and tetrahydrofurane), 5. Ketones (for example acetone, methyl ethyl ketone, methyl propyl ketone, methyl isobutyl ketone, cyclopentanone and cyclohexanone) and 6. Amines (for example primary, secondary and tertiary aliphatic amines, for example mono-, di- and triethylamine, isopropylamine, tert.-butylamine, cyclohexylamine, morpholine and ethanolamine, and heterocyclic amines, such as pyridine and imidazole) and their salts.

Carboxylic acids and their derivatives and phosphorus compounds are particularly preferred; dimethylformamide, acetic acid and phosphoric acid are especially preferred.

The sulphonation auxiliary can be used in an amount from 0.5 to 10 mol%, preferably from 1 to 8 mol% and especially from 2 to 5 mol%. In general, all or some of it can be initially introduced at the start of the reaction. The portion which has optionally not been added is then added dropwise or in portions during the further course of the first reaction stage.

In the process according to the invention, for example, the chlorosulphonic acid is initially introduced in the first process stage, together with the sulphonation auxiliary, and the aromatic compound is added at a rate depending on the rate of reaction, which can be determined using the evolution of hydrogen chloride.

In general, the chlorosulphonic acid is employed in approximately stoichiometric amounts, relative to the number of sulphonic acid chloride groups to be introduced. However, it can be advantageous to employ a slight excess of up to 20 mol%, and in particular of up to 5 mol%.

The reaction mixtures of the aromatic compound and chlorosulphonic acid in an approximately stoichiometric ratio are usually liquid and above all easily stirrable within the temperature range from 30° to 130° C. indicated, even after the reaction has ended, so that although it is possible to use an organic or inorganic solvent which is inert towards chlorosulphonic acid, this is usually not required. The reaction with the thionyl chloride can therefore be carried out subsequent to the first process step, optionally also without adding a solvent, so that the process according to the invention can be carried out as a "one-pot process."

Possible solvents or diluents which are optionally employed are: liquid sulphur dioxide, sulphonyl chloride, hydrocarbons and halogenohydrocarbons, in particular alkanes and halogenoalkanes, such as chloroform, carbon tetrachloride, methylene chloride, di-, tri- and tetra-chloroethylene, di-, tri-, tetra- and pentachloroethane, 1,1,2-trichloro-1,2,2-trifluoroethane and tetrafluoroethylene.

In general, the first stage of the process according to the invention is carried out in the temperature range from about 0° to 150° C., preferably from 10° to 140° C. and particularly preferably from 20° to 100° C.

If the reaction temperature is higher than the temperature under reflux conditions under normal pressure, the reaction is appropriately carried out under a pressure which corresponds to the vapour pressure of the reaction mixture under the particular conditions chosen.

Up to about 100° C., one can carry out the reaction under normal pressure by metering in the liquid aromatic compound or by passing in the gaseous aromatic compound, without relatively large amounts of the aromatic compounds escaping via a reflux condenser, which is appropriately used.

After the reaction has ended, it can be appropriate to remove any unreacted aromatic compound from the reaction, for example by distillation.

In the second process stage of the process according to the invention, the thionyl chloride is used in excess, relative to the aromatic compound employed. In general, one can use an amount of up to 5 mols of thionyl chloride, preferably from 1.2 to 3 mols and in particular from 1.5 to 2 mols, of thionyl chloride, relative to each sulphonic acid chloride group to be introduced.

It is not necessary to use specially purified thionyl chloride for the process according to the invention.

In general, the reaction with thionyl chloride is carried out at temperatures from 30° to 150° C., preferably from 50° to 130° C. and particularly preferably from 60° to 120° C.

It is generally advantageous to control the rate of reaction by regulating the rate of dropwise addition of the thionyl chloride.

The reaction with thionyl chloride can preferably be carried out under normal pressure, but also under reduced or elevated pressure up to 10 bars, in particular up to about 5 bars.

It can be advantageous to wash the off-gases formed in the process according to the invention with chlorosulphonic acid, for example in a bubble column. The temperature of the chlorosulphonic acid here is generally kept in the range from 0° to 80° C., in particular from 30° to 70° C.

If the wash chlorosulphonic acid is recycled to the next reaction sequence, appropriately higher average yields result since any proportions of the aromatic compounds which are entrained with the off-gases and then washed out by chlorosulphonic acid are not lost. Advantageously, an off-gas is thus obtained from which the aromatic compounds have been separated off and which therefore can be more easily worked up.

After the reaction has ended, which can be established by the fact that the evolution of gas has ended, or using known analytical methods, the excess thionyl chloride, if appropriate the solvent and any unreacted aromatic compound or unreacted chlorosulphonic acid is separated off, for example, preferably, by distillation. If necessary, the aromatic sulphonic acid chloride which remains can be purified, for example by distillation or crystallisation.

In a preferred preparation, for example of benzenesulphonyl chloride or diphenyl ether-disulphonyl chloride, one can with respect to stage 1, (a) initially introduce the aromatic compound, optionally together with the sulphonation auxiliaries, all or some of the latter being added, and add the chlorosulphonic acid, if appropriate with the remainder of the auxiliaries, at a rate depending on the rate of reaction, or (b) in a preferred procedure, initially introduce the chlorosulphonic acid and if appropriate the sulphonation auxiliaries, in each case all or some of the compounds being added, and add the aromatic compound, if appropriate together with the rest of the chlorosulphonic acid and the auxiliaries, at a rate depending on the rate of reaction.

In the preparation of benzenesulphonyl chloride, stage 1 is preferably carried out at 20°–80° C., in particular at 40°–70° C.

Surprisingly, a decrease in the sulphone formation with a simultaneous increase in yield of benzenesulphonyl chloride is found for the entire reaction (stage 1 and stage 2) if the reaction in stage 1 is carried out in the presence of sulphonation auxiliaries at elevated temperature. On the other hand, the yield of benzenesulphonyl chloride falls at elevated temperature in the absence of sulphonation auxiliaries.

The process according to the invention can be carried out either discontinuously or continuously with respect to the individual stages. Improved yields, relative both to the aromatic compound and, in particular, to the chlorosulphonic acid, are advantageously obtained by the process according to the invention.

The dilute acid unavoidably obtained and the ecological problems associated therewith largely disappear through the process according to the invention. Excess thionyl chloride, if appropriate solvent and any unreacted chlorosulphonic acid or unreacted aromatic compounds, the recycling of which is possible, are distilled off and the aromatic sulphonic acid chloride formed is then obtained from the residue.

EXAMPLES 1 TO 14

Benzenesulphonyl chloride

A flask is provided with a stirrer, dropping funnel, internal thermometer and reflux condenser with an off-gas line, optionally via a gas-washing bottle.

The chlorosulphonic acid and, optionally, the particular sulphonation auxiliary are initially introduced and benzene is slowly added dropwise at the temperature indicated in Table I in the course of 4 hours. The mixture is subsequently stirred until the evolution of gas has ended, whilst maintaining the temperature.

Thionyl chloride is then gradually added to the reaction mixture at 70°–75° C. and the mixture is stirred at this temperature until the renewed evolution of gas has ended.

The excess thionyl chloride and any unreacted benzene are distilled off in a rotary evaporator under about 100 mm Hg.

The residue which remains is distilled over a distillation bridge under 5–10 mm Hg. Table I shows the yields obtained in each case. According to analysis by gas chromatography, the content is always better than 99 percent.

In Examples 1 to 3 and 12, the entire off-gases of the reaction are washed with chlorosulphonic acid having a temperature of 30° C. A proportion of this wash chlorosulphonic acid is then also employed in a second reaction sequence carried out in the same manner. The yield resulting from this can be seen from Table I.

The distillation residues are treated with warm alkali. The insoluble constituent is diphenyl sulphone.

| Example No. | ClSO$_3$H (mols) | Benzene (mols) | SOCl$_2$ (mols) | Nature of the addition | (mols) | Sulphonation temperature °C. | Sulpho-chloride % of theory+ | Sulphone % of theory |
|---|---|---|---|---|---|---|---|---|
| 1 | 3.15++ | 3 | 6 | dimethylformamide | 0.15 | 70 | 91.5+++ | 5.0 |
| 2 | 3.15++ | 3 | 6 | dimethylformamide | 0.09 | 70 | 90.7 | 6.6 |
| 3 | 1.05++ | 1 | 2 | dimethylformamide | 0.05 | 100 | 84.9 | 8.5 |
| 4 | 1.05 | 1 | 2 | dimethylformamide | 0.05 | 70 | 89.8 | 4.3 |
| 5 | 1 | 1 | 2 | dimethylformamide | 0.05 | 70 | 87.5 | 4.5 |
| 6 | 1 | 1 | 2 | CH$_3$COOH | 0.05 | 70 | 85.8 | 5.2 |
| 7 | 1 | 1 | 2 | H$_3$PO$_4$ | 0.05 | 80 | 85.2 | 6.9 |
| 8 | 1 | 1 | 2 | dimethylformamide | 0.05 | 20 | 84.0 | 9.2 |
| 9 | 1 | 1 | 2 | dimethylformamide | 0.10 | 70 | 80.4 | 3.4 |
| 10 | 1 | 1 | 2 | dimethylformamide | 0.02 | 70 | 84.0 | 7.1 |
| 11 | 1 | 1 | 2 | dimethylformamide | 0.01 | 70 | 76.0 | 8.1 |
| 12 | 1.05++ | 1 | 1 | — | — | 20 | 83.5 | 14.7 |
| 13 | 1 | 1 | 2 | — | — | 20 | 79.1 | 14.4 |

| Example No. | ClSO₃H (mols) | Benzene (mols) | SOCl₂ (mols) | Nature of the addition | (mols) | Sulphonation temperature °C. | Sulpho-chloride % of theory[+] | Sulphone % of theory |
|---|---|---|---|---|---|---|---|---|
| 14 | 1 | 1 | 2 | — | — | 70 | 73.7 | 17.4 |

[+] relative to benzene employed
[++] also using "wash chlorosulphonic acid (see the description of the experiment)
[+++] average result from 5 experiments, fluctuation limits 90.7 to 94.3% of theory.

EXAMPLES 15 TO 25

The aromatic compounds given in Table II are reacted in a standardised procedure corresponding to Example 5 according to the procedure described in Examples 1 to 14.

The temperature in stage 1 (reaction with chlorosulphonic acid) and stage 2 (reaction with thionyl chloride) is 70° C. in each case. 5 mol% of dimethylformamide of the sulphonation auxiliary are employed in each case.

Since a standardised procedure was followed, Examples 15 to 25 are not optimised with respect to the temperature control.

| Example No. | Aromatic compound | | ClSO₃H | | SOCl₂ | | Aromatic sulphonic acid chloride | | |
|---|---|---|---|---|---|---|---|---|---|
| | | [g] | [mols] | [g] | [mols] | [g] | | Purity[+] | % of theory |
| 15 | toluene | | | | | | | toluenesulphonyl chloride | |
| | | 92 | 1 | 1 | 2 | 153 | | 30.0% of o- 70.0% of p- | 80 |
| 16 | cumene | | | | | | | 4-isopropyl-benzenesulphonyl chloride | |
| | | 120 | 1 | 1 | 2 | 193 | | 94.4 | 83 |
| 17 | tetralin | | | | | | | 1,2,3,4-tetrahydronaphthalene-6-sulphonyl chloride | |
| | | 132 | 1 | 1 | 2 | 195 | | 86.5% 11.1% of isomer | 71 9 |
| 18 | p-xylene | | | | | | | 2,5-dimethyl-benzenesulphonyl chloride | |
| | | 106 | 1 | 1 | 2 | 177 | | 99.0 | 86 |
| 19 | diphenylmethane | | | | | | | diphenylmethane-4,4'-disulphonyl[++] chloride | |
| | | 168 | 1 | 2 | 4 | 224 | | melting point 121° C. | 61 |
| 20 | diphenyl | | | | | | | 4,4'-diphenyldisulphonyl chloride[++] | |
| | | 154 | 1 | 2 | 4 | 218 | | melting point 200° C. | 62 |
| 21 | o-chloro-toluene | | | | | | | 2-chloro-toluene-5-sulphonyl chloride | |
| | | 127 | 1 | 1 | 2 | 187 g | | 78.6 16.1 of isomer | 65 13 |
| 22 | 2,6-dichloro-toluene | | | | | | | 2,4-dichloro-3-methyl-benzenesulphonyl chloride | |
| | | 161 | 1 | 1 | 2 | 179 | | 91.0 | 63 |
| 23 | chlorobenzene | | | | | | | p-chloro-benzenesulphonyl chloride | |
| | | 113 | 1 | 1 | 2 | 189 | | 99.3 | 89 |
| 24 | fluorobenzene | | | | | | | p-fluoro-benzenesulphonyl chloride | |
| | | 96 | 1 | 1 | 2 | 164 | | 96.0 | 81 |
| 25 | o-dichlorobenzene | | | | | | | 3,4-dichloro-benzenesulphonyl chloride | |
| | | 147 | 1 | 1 | 1 | 200 | | 98.5 | 80 |

[+] according to analysis by gas chromatography
[++] recrystallisation instead of distillation because of the high boiling point

EXAMPLE 26

114 g of chlorosulphonic acid (66 cm³) and 85 g of diphenyl ether, dissolved in 50 cm³ of ethylene chloride (132 cm³), are simultaneously added dropwise to 5 g of chlorosulphonic acid in 120 cm³ of ethylene chloride at 50° in the course of one hour. The mixture is subsequently stirred at 50° C. for 30 minutes, 300 g of thionyl chloride (2.52 mols=excess of 1.52 mols) are allowed to run in at this temperature in the course of 90 minutes and the mixture is heated under reflux at 80°–85° for 6 hours. Excess thionyl chloride and ethylene chloride are distilled off up to a sump temperature of 130°–140° C., finally under 10 mm Hg. The product, which is discharged as a liquid onto a metal sheet, is allowed to solidify and is ground and dried at 40° in vacuo. Yield: 178 g=97% of theory, melting point 123.5°–128°. Thin layer chromatography: 0.1% of monosulphochloride and 2.0% of unknown by-products.

What is claimed is:

1. In a process for the preparation of a sulphonic acid chloride of the formula

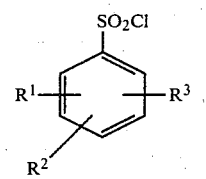

wherein R¹, R² and R³ are identical or different and denote hydrogen, a lower alkyl radical or a cycloalkyl radical, halogen, aryl, aralkyl, aryl ether or a radical —SO₂Cl, —SO₂aryl,

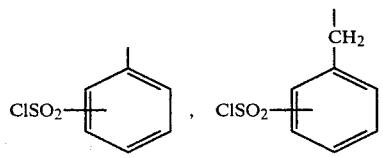

-continued

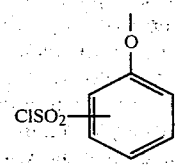, or

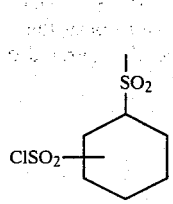

or wherein adjacent radicals $R^1$ and $R^2$ are linked to form a cycloaliphatic, aromatic or hetero-aromatic ring which is optionally substituted by a sulphonic acid chloride group which consists essentially of contacting an aromatic compound of the formula

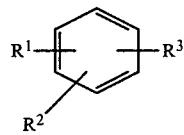

wherein $R^1$, $R^2$ and $R^3$ have the above-described meaning with chlorosulphonic acid and thionyl chloride, the improvement which consists essentially of contacting said aromatic compound with chlorosulphonic acid which acid is present in an excess up to 20 weight percent, relative to each sulphonic acid chloride group to be introduced on the aromatic ring, the chlorosulphonic acid being introduced initially into a reaction vessel and the aromatic compound being added thereto depending upon the rate of reaction whereby the reaction product contains aromatic sulphonic acid, unreacted chlorosulphonic acid, sulfuric acid, a diphenylsulfone, hydrogen chloride and unreacted aromatic compound and thereafter contacting said reaction product with excess thionyl chloride.

2. A process according to claim 1 wherein the reaction of the aromatic compound with the chlorosulphonic acid is carried out in the absence of thionyl chloride.

3. A process according to claim 1 wherein the reaction of the aromatic compound with chlorosulphonic acid is carried out in the presence of a solvent.

4. A process according to claim 1 wherein the reaction of the chlorosulphonic acid and thionyl chloride is carried out in the presence of a sulphonation auxiliary.

5. A process according to claim 1 wherein the aromatic compound and chlorosulphonic acid are employed in a stoichiometric amount.

6. A process according to claim 1 wherein the reaction mixture obtained in the first stage is reacted in a second stage with thionyl chloride in an amount of up to 5 equivalents, relative to each sulphonic acid chloride group to be introduced.

7. A process according to claim 1 wherein off-gases are removed from the process, the off-gases are continuously washed with chlorosulphonic acid and the chlorosulphonic acid thus obtained is recycled to the process.

8. A process according to claim 1 wherein the reaction of the aromatic compound with chlorosulphonic acid is carried out at a temperature between 0° and 150° C.

9. A process according to claim 1 wherein the reaction of the aromatic compound with chlorosulphonic acid is carried out at a temperature between 10° to 140° C.

10. A process according to claim 1 wherein the reaction of the aromatic compound with chlorosulphonic acid is carried out at a temperature between 20° to 100° C.

11. A process according to claim 8 wherein the reaction with thionyl chloride is carried out at a temperature between 30° and 150° C.

12. A process according to claim 11 wherein 1.2 to 3 mols of thionyl chloride are employed relative to each sulphonic acid chloride group to be introduced.

13. In a process for the preparation of a sulfonic acid chloride of the formula

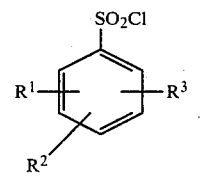

wherein $R^1$, $R^2$ and $R^3$ are identical or different and denote hydrogen, a lower alkyl radical or a cycloalkyl radical, halogen, aryl, aralkyl, aryl ether or a radical $-SO_2Cl$, $-SO_2aryl$, or wherein adjacent radicals $R^1$ and $R^2$ are linked to form a cycloaliphatic, aromatic or hetero-aromatic ring which is optionally substituted by a sulfonic acid chloride group which comprises contacting an aromatic compound of the formula wherein $R^1$, $R^2$ and $R^3$ have the above-described meanings with chlorosulfonic acid and thionyl chloride, the improvement which comprises initially contacting at an elevated temperature said aromatic compound with chlorosulfonic acid in the presence of a sulfonation auxiliary, said chlorosulfonic acid being present in an excess of up to 20 mol percent relative to each sulfonic acid chloride group to be introduced on the aromatic ring and thereafter adding to the reaction product obtained therefrom excess thionyl chloride.

14. A process according to claim 13 wherein the reaction of the aromatic compound with chlorosulfonic acid is carried out in the absence of thionyl chloride.

15. A process according to claim 14 wherein the aromatic compound and chlorosulfonic acid are employed in an approximately stoichiometric amount.

16. A process according to claim 15 wherein the reaction of the aromatic compound with chlorosulfonic acid is carried out at a temperature up to 150° C.

* * * * *